United States Patent
Curcio

(10) Patent No.: US 7,854,827 B2
(45) Date of Patent: Dec. 21, 2010

(54) COMPARATIVE MULTIDIMENSIONAL GEL ELECTROPHORESIS

(75) Inventor: Mario Curcio, Rotkreuz (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 920 days.

(21) Appl. No.: 11/642,242

(22) Filed: Dec. 20, 2006

(65) Prior Publication Data
US 2007/0151854 A1 Jul. 5, 2007

(30) Foreign Application Priority Data
Dec. 21, 2005 (EP) ................... 05028033

(51) Int. Cl.
C25B 7/00 (2006.01)
C07K 1/26 (2006.01)
C07K 1/28 (2006.01)

(52) U.S. Cl. ............... 204/610; 204/606; 204/612; 204/616; 204/618; 204/619; 204/620; 204/459; 204/466; 204/467; 204/470

(58) Field of Classification Search ............... 204/459, 204/466, 467, 470, 606, 610, 612, 616, 618, 204/619, 620
See application file for complete search history.

(56) References Cited

U.S. PATENT DOCUMENTS

| | | | |
|---|---|---|---|
| 5,795,749 A | 8/1998 | Wong et al. | |
| 6,277,259 B1 | 8/2001 | Guttman et al. | |
| 6,554,991 B1 | 4/2003 | Goodman et al. | |
| 6,599,410 B1 * | 7/2003 | Steiner et al. | 204/466 |
| 6,602,975 B2 | 8/2003 | Hubbell et al. | |
| 6,676,819 B1 * | 1/2004 | Liu et al. | 204/451 |
| 2002/0096431 A1 | 7/2002 | Sevigny et al. | |
| 2002/0170825 A1 | 11/2002 | Lee et al. | |
| 2003/0103207 A1 | 6/2003 | Kopf-Sill et al. | |
| 2003/0127331 A1 | 7/2003 | Leka | |

(Continued)

FOREIGN PATENT DOCUMENTS

EP 0366897 5/1990

(Continued)

OTHER PUBLICATIONS

Unlu M., Morgan M. E., Minden J. S. (1997). Difference gel electrophoresis: a single gel method for detecting changes in protein extracts. Electrophoresis, 18:2071-2077.

(Continued)

Primary Examiner—Bruce F Bell
(74) Attorney, Agent, or Firm—Dinsmore & Shohl LLP

(57) ABSTRACT

A device providing an arrangement for the separation of a sample mixture for analytical reasons based on multidimensional gel electrophoresis and method thereof are disclosed. The separation involves a first separation in a first dimension of the device on the basis of isoelectric points and a second separation in a second dimension of the device on the basis of molecular size. At least two gel strips for the first dimension separation step and a corresponding gel for the second dimension separation step are provided. The two gel strips are arranged on a single carrier either on the same side or on opposite sides. By having at least two gel strips arranged in such a manner at least two analytical processes can be executed in parallel on the single carrier without the use of valves.

33 Claims, 9 Drawing Sheets

U.S. PATENT DOCUMENTS

| | | | |
|---|---|---|---|
| 2003/0207806 | A1 | 11/2003 | Ensign et al. |
| 2004/0045829 | A1* | 3/2004 | Ingenhoven et al. ........ 204/465 |
| 2004/0112751 | A1 | 6/2004 | Han et al. |
| 2004/0144647 | A1 | 7/2004 | Dorner et al. |
| 2005/0043490 | A1 | 2/2005 | Klee et al. |
| 2006/0226010 | A1 | 10/2006 | Curcio et al. |
| 2007/0119712 | A1* | 5/2007 | Hadbawnik ................. 204/459 |

FOREIGN PATENT DOCUMENTS

| | | |
|---|---|---|
| WO | WO02084273 | 10/2002 |
| WO | WO03092846 | 11/2003 |
| WO | 03/101591 A1 | 12/2003 |
| WO | 2005/029061 A1 | 3/2005 |

OTHER PUBLICATIONS

Sebastiano, R., Citterio, A., Lapadula, M. & Righetti, P.G. (2003). A new deuterated alkylating agent for quantitative proteomics. Rapid Commun. Mass Spectrom., 17:2380-2386.

O'Farrell P. H. (1975). High resolution two-dimensional electrophoresis of proteins. Journal of Biological Chemistry, The American Society of Biological Chemists, Inc., ISSN 0021-9258 vol. 250, Nr. 10, pp. 4007-4021.

Li Y., et al (2004). Integration of isoelectric focusing with parallel sodium dodecyl sulfate gel electrophoresis for multidimensional protein separations in a plastic microfluidic network. Analytical Chemistry, American Chemical Society, ISSN 0003-2700, vol. 76, Nr. 3, pp. 742-748.

Herbert, et al. (2001). Reduction and alkylation of proteins in preparation of two-dimensional map analysis: Why, when, and how? Electrophoresis, vol. 22, pp. 2046-2057.

Partial European Search Report, Jul. 3, 2006 for EP Application No. 05 02 8033, pp. 1-4.

Simpson, "Proteins and Proteomics: A Laboratory Manual", CSHL Press, ISBN 0879695544, 9780879695545, published 2003, pp. 349-351.

Sobotka et al., "Advance in Clinical Chemistry", Academic Press, 1961, p. 214.

Rill et al. (Peptide separations by slab gel electrophoresis in Pluronic F127 polymer liquid crystals, Electrophoreisis 2004, 25, 1249-1254).

* cited by examiner

COMPARATIVE MULTIDIMENSIONAL GEL ELECTROPHORESIS

RELATED APPLICATIONS

This application claims priority to EP 05028033.8 filed Dec. 21, 2005.

FIELD OF THE INVENTION

The present invention refers generally to the separation of a sample mixture for analytical reasons based on multidimensional gel electrophoresis, and in particular to an improved method for electrophoresis analysis based on gel polymerization and electrokinetic equilibration without the use of valves and a system or ways for integration and automation thereof.

BACKGROUND OF THE INVENTION

Two-dimensional slab gel electrophoresis is still the most used approach to proteomics and it might be still for several years, if other limitations still present are addressed. Indeed, this remains a time-consuming and laborious procedure, requiring trained personnel, on the hands of whom the quality of results is mainly depending. Although the post-electrophoretic steps are highly robotized, the separation step is far from it, so that problems with accuracy and consistency can arise from variations in the numerous parameters to keep under control. Some of these are for example, sample loading and rehydration, in terms of sample amount, losses, and homogeneity of the strip, strip handling with risk of damaging and contamination, imprecise and slow coupling of the strip to the gel, gel casting and polymerization, in terms of homogeneity, casting and reaction speed, especially for gradients, air sensitivity, time for completion until run is started, risk to trap bubbles causing consequently also field discontinuities, increase in temperature during the run, pH and viscosity changes, and loss of buffer capacity. Lack of acceptable reproducibility, meaning that no two gel images are directly superimposable, remains therefore a major problem if considered that gels are mostly made to be compared, e.g., to detect and quantify differences in protein expression between experimental pairs of complex protein samples, i.e., each sample having more than 10 individual protein components. In practical terms, this translates in the need to run more gels to build reference maps for each condition and reach a certain degree of certainty, which in turn means even more manual work.

A technique, apparently overcoming this problem, was introduced in 1997, namely fluorescent 2-D differential gel electrophoresis (DIGE) by Unlu et al. (Unlu M., Morgan M. E., Minden J. S. (1997). Difference gel electrophoresis: a single gel method for detecting changes in protein extracts. *Electrophoresis*, 18:2071-2077). DIGE is based on the use of two mass- and charge-matched N-hydroxy succinimidyl ester derivatives of the fluorescent cyanin dyes Cy3 and Cy5, possessing distinct excitation and emission spectra, to differentially label lysine residues of two protein samples, which are then mixed and run on the same gel. Thus, matching is automatic and straightforward and in principle only a single gel could be sufficient. However, for a proper statistical evaluation, at least three to five gels are required as well. To make things even more complicated than before is the fact that very stringent labeling conditions should be followed. It is indeed well known that pre-labeling can generate a large number of positional isomers as well as partially reacted species yielding very heterogeneous results. Labeling must be therefore minimal, trying to achieve possibly the addition to a single lysine residue on the entire protein molecule. In addition, the over-reacted species might precipitate as a result of an acquired increased hydrophobicity, but the biggest issue is the fact that one cannot simply run a DIGE gel and cut out the spots of the differentially expressed proteins for subsequent mass spectroscopy (MS) analysis. Indeed, there is no way to predict to which lysine, thus to which peptide of the digested spot, the covalent fluorescent label will be attached, so that peptide identification might be problematic. Moreover, after the gel has been removed from the fluorescence scanner, the spots will no longer be visible, so that a protein dye or other visual staining technique should be thus used anyway for the post-electrophoretic visualization. Finally, perhaps the biggest limitation is represented by the very high cost of the equipment, software and reagents.

Automation associated with better reproducibility are the main strengths of the instrumental chromatographic approach, as no further manual intervention is required after the sample has been loaded. Nevertheless, this is true only when using the same column and running the same method sample after sample in a sequential order. Columns of the same size packed with the same material might give indeed different elution times, as column packing is per se not perfectly reproducible. New materials such as, e.g., monoliths, bring with them new advantages but columns are still made one by one, meaning that, in analogy to gels, no two chromatograms run in parallel are superimposable. Besides this, limitations due to cost and complexity of instrumentation make this approach after all not faster and not really more convenient, despite other inherent advantages like on-line detection and the possibility of direct coupling to MS. Gels, on the other hand, can be easily run in parallel, can offer under optimal conditions superior resolution, and can be directly compared by imaging. The potential is therefore still very big if integration and automation, thus higher reproducibility and throughput, are achieved for gels too, allowing to run more and comparable gels in less time with less work and reduced costs.

SUMMARY OF THE INVENTION

It is against the above background that the present invention discloses advantageous embodiments for multidimensional gel electrophoresis, providing convenient and effective means of achieving parallel analysis and comparative studies based on fast UV gel polymerization and SDS electrokinetic equilibration without the use of valves.

According to a first aspect of the present invention, a device providing an arrangement for separation of a complex protein sample based on multidimensional gel electrophoresis without the use of valves is disclosed. The separation involves a first separation of the sample on the basis of isoelectric points and a second separation of the sample on the basis of molecular size. The device comprises at least two first gel strips providing the first separation in a first dimension of the device, and a gel in contact with each of the at least two first gel strips and providing the second separation in a second dimension of the device. A single carrier supports the first gel strips and the gel such that at least two analytical processes, each involving the first separation and the second separation, can be executed in parallel on the single carrier.

According to a second aspect of the present invention, a method for separation of a complex protein sample based on multidimensional gel electrophoresis without the use of valves is disclosed. The separation involves a first separation of the sample on the basis of isoelectric points and a second separation of the sample on the basis of molecular size. The method comprises providing the first separation in a first dimension using at least two first gel strips, and providing the second separation in a second dimension using a gel in contact with each of the at least two first gel strips. The method further comprises supporting the first gel strips and the gel on a single carrier such that at least two analytical processes, each involving the first separation and the second separation, can be executed in parallel on the single carrier.

Further possible embodiments of the inventive arrangement are described within the claims and are described in more details within the following examples with reference to the attached drawings.

BRIEF DESCRIPTION OF THE DRAWINGS

The following detailed description of the embodiments of the present invention can be best understood when read in conjunction with the following drawings, where like structure is indicated with like reference numerals and in which:

FIGS. 4a and 4b are diagrams showing a valve arrangement provided to a strip, wherein FIG. 4a shows a lowered fitting bar, and FIG. 4b shows the fitting bar raised to shape a gap above the strip.

FIGS. 9a and 9b are block diagrams, shown in cross section, of another embodiment according to the present invention, which is shown in a "symmetric gels" form, and in which FIG. 9a shows the arrangement according to the present invention in a longitudinal section during the separation of the sample in the first and the second dimension, and FIG. 9b shows the gel strips after finishing the separation for analytical reason with the possibility to compare simultaneously the separation of two samples.

FIGS. 11a and 11b are block diagrams showing still another embodiment according the present invention which allows extension from two- to three-dimensional analyses, in which FIG. 11a shows the embodiment for the first dimension separation in cross sectional view and FIG. 11b shows the embodiment for the first separation in a top view.

Figure 1:
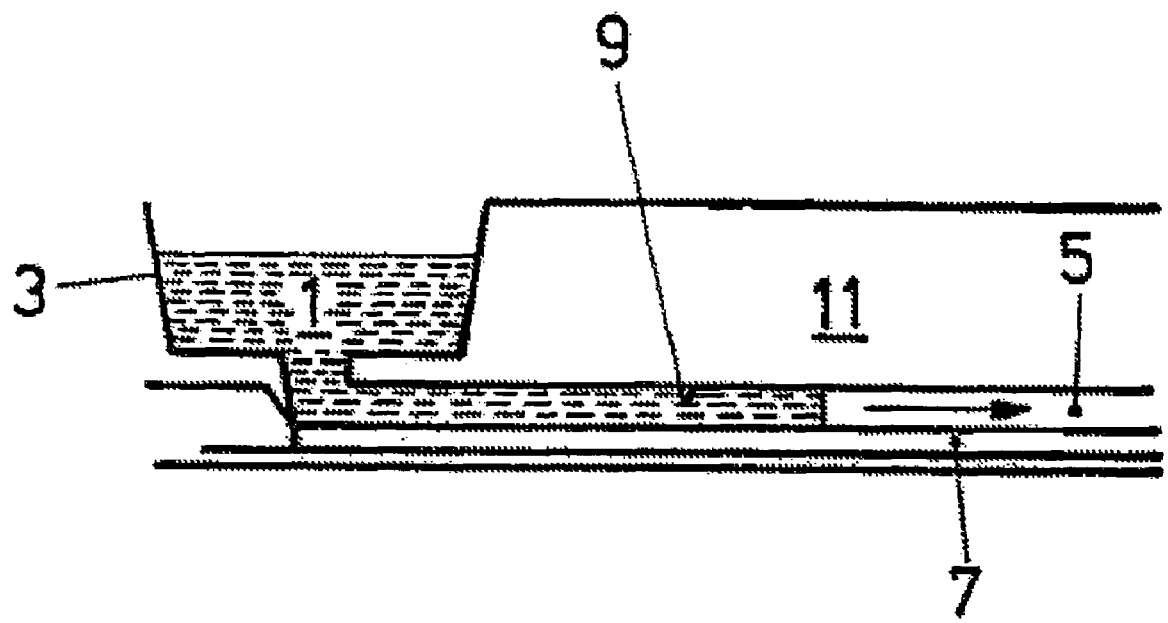
FIG. 1 is a diagram showing a longitudinal section part of a first gel strip arranged within a 2D gel electrophoresis device or disposable respectively.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DESCRIPTION OF THE INVENTION

Automation associated with better reproducibility are the main strengths of the instrumental chromatographic approach, as no further manual intervention is required after the sample has been loaded. Nevertheless, this is true only when using the same column and running the same method sample after sample in a sequential order. Columns of the same size packed with the same material might give indeed different elution times, as column packing is per se not perfectly reproducible. New materials such as, e.g., monoliths, bring with them new advantages but columns are still made one by one, meaning that, in analogy to gels, no two chromatograms run in parallel are superimposable. Besides this, limitations due to cost and complexity of instrumentation make this approach after all not faster and not really more convenient, despite other inherent advantages like on-line detection and the possibility of direct coupling to a mass spectrometer. Gels, on the other hand, can be easily run in parallel as disclosed thereinafter, can offer under optimal conditions superior resolution, and can be directly compared by imaging. The potential is therefore still very big if integration and automation, thus higher reproducibility and throughput, are achieved for gels too, allowing to run more and comparable gels in less time with less work and reduced costs.

In co-pending and commonly owned U.S. patent application Ser. No. 11/278,975 (hereinafter referred to as "the '975 application"), the disclosure of which is herein incorporated fully by reference, a modification of the general method based on the combination between sodium dodecyl-sulfate (SDS) equilibration, and fast UV polymerization is disclosed, which portions thereof are recalled and described again below.

For simplification reasons and for the better understanding of the invention disclosed by the '975 application, the various method or process steps for the two-dimensional gel electrophoresis analysis are described in operational sequence. Below is a brief list of the steps involved during the execution of the developed method followed by a discussion for each of them:

1. Perform reduction/alkylation prior to isoelectric focusing (IEF).
2. Load sample.
3. Run IEF in any of the following proposed ways.
4. Increase spacing between strip and opposite surface of the gel mold.
5. Bring gel solution for 2nd dimension separation while achieving coupling at the same time and polymerize.
6. Bring SDS to the focused proteins electrokinetically.
7. Replace running buffer and run 2nd dimension.
8. Open gel mold to remove gel.
9. Proceed with fixing and staining.

Within the following description of the various steps reference is also made to the attached FIGS. 1-7, in which examples of possible embodiments and parts of the developed system or device respectively according the '975 application are shown.

Step 1

Reduction/alkylation is performed just before sample loading as the last step of the sample preparation according to Sebastiano et al. (Sebastiano et al. (2003). *Rapid Commun. Mass Spectrom.* 17:2380-2386). Same reducing and alkylating reagents, i.e., tributylphosphine (TBP) and vinyl pirydine (VP) are used in one embodiment, although with a slight modification of the method. It has been found that it is not necessary to buffer the sample solution for the alkylation reaction to occur, thus avoiding a useless increase of the salt concentration that would result in high current and longer isoelectric focusing (IEF) times unless desalting is carried out. Moreover, it is considered more efficient to add TPB and VP in two consecutive steps rather than simultaneously since the two reagents can react with each other. In this way, shorter reaction times, e.g., overall 30 min, are also needed. As an example, a typical solution used to solubilize the protein sample, with variations of course allowed, consists of:

| Thiourea | 2 M |
|---|---|
| Urea | 7 M |
| CHAPS | 2% (w/v) |
| Bio-Lyte ® 3/10 Ampholytes | 0.5% (v/v) |
| Bromophenol Blue | 0.002% (w/v) |
| 1,2-propandiol | 20% |

To this, TBP is added, e.g., first in concentration of 5 mM for about 10 min, followed by addition of VP 20 mM final concentration for about 20 min and again TBP in sufficient molar amount to quench the excess of the previous reagent, rather than a different reducing agent such as dithioerythritol (DTE).

The function of the 1,2-propandiol, which is a favorite additive among others possible such as, e.g., glycerol, PEG, diethylenglycole, is to minimize electroosmotic flow (EOF) during IEF while maintaining the viscosity of the sample solution low, which is important for the sample loading step as will be seen below.

Step 2

The sample, e.g., in the solution above, is inserted such as, e.g., pipetted into a small sample well from which the sample can get in contact with the strip and the internal surface of the disposable body directly facing the strip and be guided as proposed according to the present invention by capillary hydrophilic forces between such surface and the semi-dry strip filling entirely the volume so defined and shown in FIG. 1. FIG. 1 shows in longitudinal section part of the first gel strip as disclosed in the '975 application arranged within a 2D gel electrophoresis device or disposable respectively. The sample 1 as described above is inserted in a sample well 3 and is guided along a capillary opening 5 along the hydrophilic gel strip 7 in the direction of the shown arrow. In one embodiment, but not necessarily, the area in correspondence of the strip is hydrophilic, while at least part of the rest of the surface 9 of the disposable body 11 is, or coated with, a hydrophobic or otherwise non gel sticking material. Contribution to sample guiding might be given simply also by two drawn parallel lines on the disposable body reproducing the size of the strip underneath. Gel sticking might be desirable on the same cover plane where the strip is attached, which can then be all hydrophilic or have gel bond properties. If this is, e.g., a foil, the advantage is that at the end it can be peeled together with the gel, making handling easier and minimizing the risk of breakage. Pressure or vacuum may be employed to assist the loading but can in general be avoided. In this controlled way, a volume of sample corresponding exactly to the amount needed to rehydrate the strip can be introduced minimizing waste.

Step 3

Figure 2:
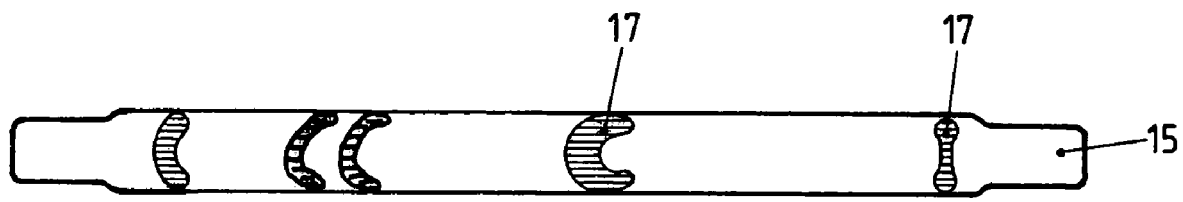
FIG. 2 shows a pluronic strip with the separately located protein components after an isoelectric focusing step.
Figure 3:
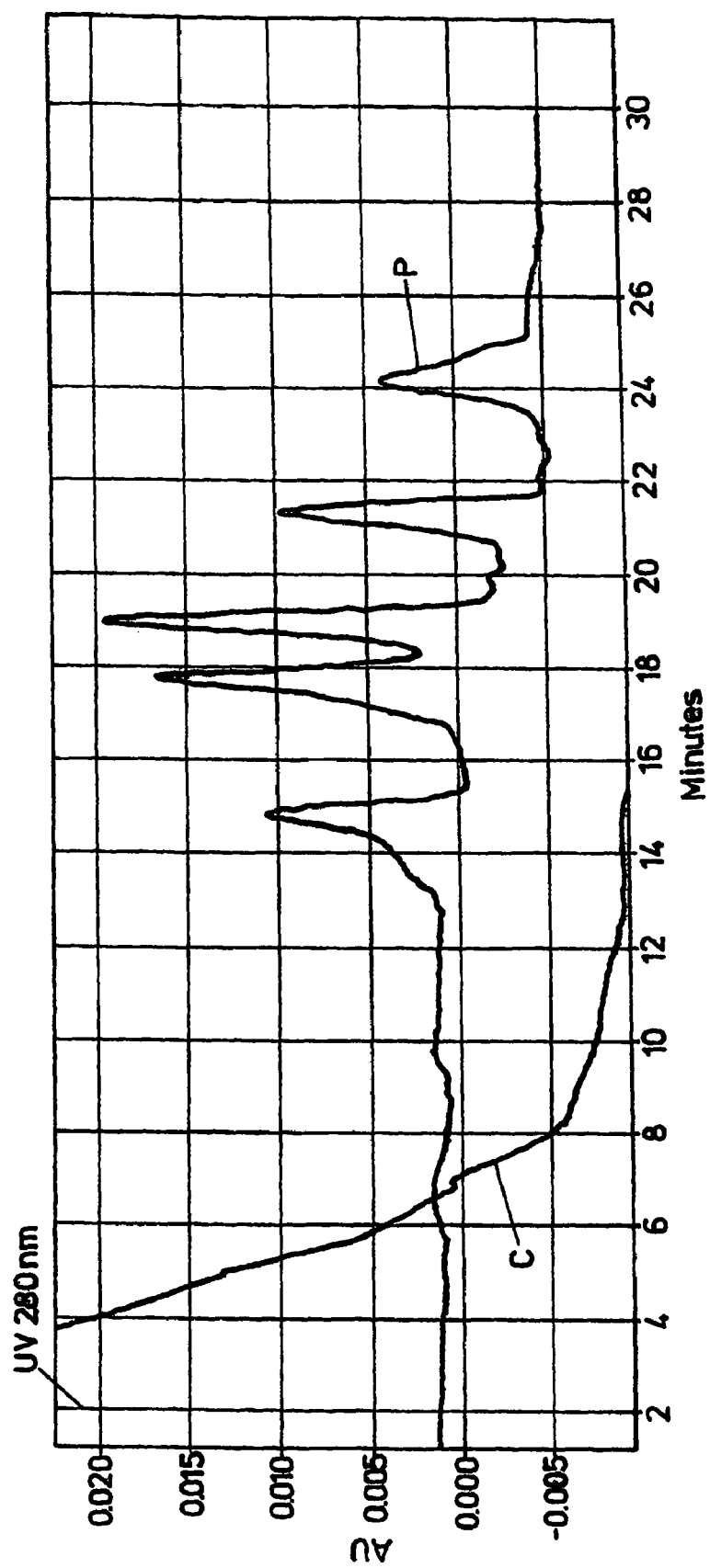
FIG. 3 is a form separation plot of a sample by capillary IEF in a pluronic filled capillary, wherein line C represents current drop during IEF while line P shows the IEF peaks following mobilization.

To be noticed is the fact that the strip 7 has not to be closed at its sides by any valves. Evaporation is minimized because the gel mold is nearly closed at all sides and because temperature in one embodiment is kept cool during IEF being the disposable positioned, e.g., on a cooling plate. Commercially available strips can be used, which would be already integrated in the closed compact disposable or otherwise separately supplied attached to the cover, which would close the main disposable body. Strips may also be polymerized in situ using the same system of hydrophilic guiding, this time on both surfaces, or otherwise a hydrophilic neutral porous material, e.g., a membrane with a strip shape. In this case, however, instead of passive rehydration we would have an active sample loading. Disclosed is also a new IEF medium, which might be premixed with the sample solution, guided as above to assume a strip shape and capable of gelling when increasing the temperature slightly above room temperature. A medium with this characteristic is a block copolymer of ethylene oxide and propylene oxide belonging to the class of commercially available products known as Pluronics® from BASF (Mount Olive, N.J., USA). A possibly suitable one is, e.g., Pluronic® F127 at a concentration of about 20% or above when mixed with a sample solution such as that described above. This product besides other commercial applications has already been used as efficient sieving medium in capillary electrophoresis of oligonucleotides and sometimes of peptides but was never used for IEF of proteins. A normal characteristic of this copolymer when dissolved in water solution at a critical concentration is to be liquid at low temperature, typically <5° C. and become a sort of liquid crystalline gel at room temperature. The presence of urea, thiourea, ampholytes and detergents in the sample solution shifts the gelling point above 30-35° C., thus making the liquid, although viscous, easy to handle and guide at room temperature. Both in capillary electrophoresis and in the shape of a strip it was possible to obtain nicely focused proteins as shown in FIGS. 2 and 3. FIG. 2 shows a pluronic strip 15 with the separately located protein components 17 after the isoelectric focusing step. FIG. 3 shows in diagram form the separation of the same sample by capillary IEF in a pluronic filled capillary. Here, the line C represents the current drop during IEF while the line P shows the IEF peaks following mobilization. The advantage in capillary electrophoresis is that uncoated capillaries can be used due to the dynamic coating properties of the polymer itself.

Step 4

Figure 4A:
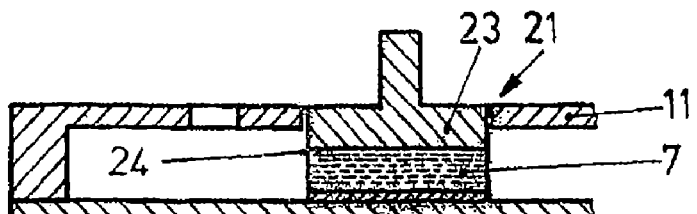
Figure 4B:
Figure 5B:
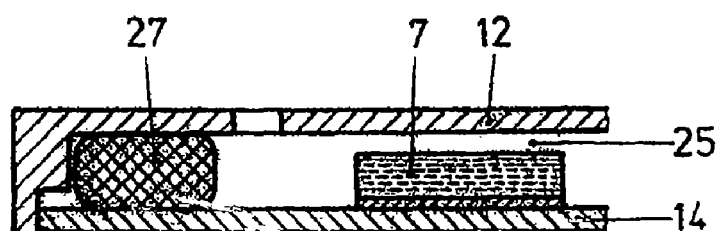
FIGS. 5a and 5b are diagrams showing another arrangement wherein a strip is attached either on a rigid or elastic component as shown by FIG. 5a, and which moves to bring the strip in contact with a frame as shown in FIG. 5b.
Figure 5A:
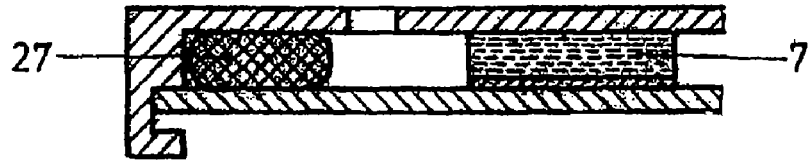
Figure 6B:
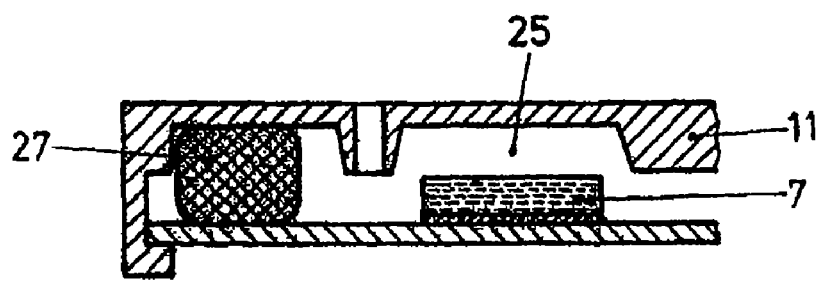
FIGS. 6a and 6b are diagrams showing still another arrangement wherein a strip is attached either on a rigid or elastic component as shown by FIG. 5a, and wherein a cavity or a gap is shaped between the gel strip and frame as shown by FIG. 6b, which when compressed as shown in FIG. 6a the air volume around the strip is reduced.
Figure 6A:
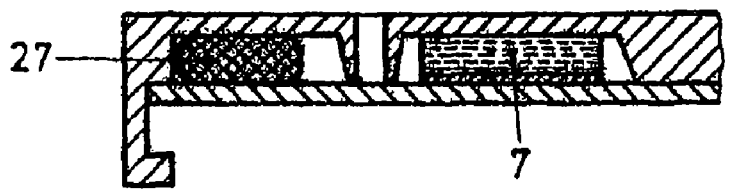

A problem experienced, at least with commercial strips, is represented by an irreproducible second dimension when the strip and the second dimension gel, polymerized directly in contact with the strip, have the same thickness. On one hand a spacing of the mold corresponding to the thickness of the rehydrated strip is necessary in order to introduce the right amount of sample, rely on a good capillary force and perform a good first dimension analysis. On the other hand a small space above the strip is required to achieve proper coupling with the gel and perform a good second dimension analysis. To solve this problem, three possible solutions are shown schematically in FIGS. 4 to 6, where by way of a cross-sectional view part of the analytical disposable is shown in the area of the first gel strip 7. One way is to have constant thickness for the gel mold and change thickness only in correspondence of the strip. For example, one can have a slit 21 in the disposable body 11 where a fitting bar 23 with a hydrophilic bottom 24 is automatically lowered and raised accordingly with two allowed positions as shown in FIGS. 4a and 4b. FIG. 4b shows the raised fitting bar 23 to shape a gap 25 above the strip 7. But other variants are possible, where e.g., the strip to move is attached either on a rigid or elastic component. Another way is to change the spacing of the entire gel mold between two allowed positions. For this purpose an elastic compressible frame 27—"O"-ring-like—can be inserted between two mold planes 12 and 14, as shown in FIGS. 5a and 5b and for these different geometries could be drawn. Eventually the two planes 12 and 14 can be brought to touch each other when the frame is squeezed as shown in FIG. 5a, while a cavity or a gap 25 is shaped between the upper mold plane 12 and the gel strip 7 when the compressible frame is expanded, as shown in FIG. 5b. A suitable cavity 25 with the same height of the strip 7 can be left in correspondence of the strip such as schematically drawn in FIG. 6. Again, FIG. 6a shows the compressible frame squeezed, while FIG. 6b shows the compressible frame in expanded condition. The mechanism of sample loading is in one embodiment still the same but the air volume around the strip would be reduced.

Step 5

For more controllable gel casting this step in one embodiment is carried out vertically, which means that the instrument will operate a 90° rotation of the disposable. The introduction of the gel solution can occur through proper tubing fitting or needle either from the bottom to the top or from the top to the bottom and the strip may find itself located at any of the four sides relative to the vertical mold. In this way the gel solution will fill completely the mold, at least partially contacting, covering and/or enclosing the strip in one embodiment, in order to maintain the resolution of the first dimension and diffusion of acrylamide inside the strip, with possible crosslinking to the sample, so that polymerization occurs rapidly. For this reason the traditional method, making use of ammonium persulfate (APS) and N,N,N',N'-tetramethylethylenediamine (TEMED) as initiator and catalyst respectively of radical polymerization, is not preferred because these reagents have to be added and mixed at the last moment as they start immediately polymerization already during casting and because the reaction proceeds slowly taking normally more than one hour to be completed. Ideally, the gel solution contains already the reagents for polymerization and is stable under storage conditions; important is also that once the reaction is triggered, e.g., by external energy source, this proceeds fast, while maintaining the characteristics of the traditional sieving gel. This can be achieved for instance by UV-initiated polymerization choosing an initiator that is stable in the acrylamide gel solution until exposed to a light source whose wavelength range comprises its absorbance spectrum. UV transparent materials should be thereby used for the disposable. As these compounds are generally not polar, hence poorly soluble in aqueous solution, a modification of the gel solution is necessary. For example up to 10% diethylenglycole without compromising the performance of the gel can be used. A suitable initiator is for example 2,2'-dimethoxy-2-phenyl-acetophenone (DMPA) at concentration of 0.05% or below. By this, exposure of the gel mold to UVA light of sufficient power results in complete polymerization in less than 5 min.

Although photopolymerization itself is not new, it was never applied to our knowledge to two-dimensional gel based proteomics.

Steps 6 and 7

Figure 7:
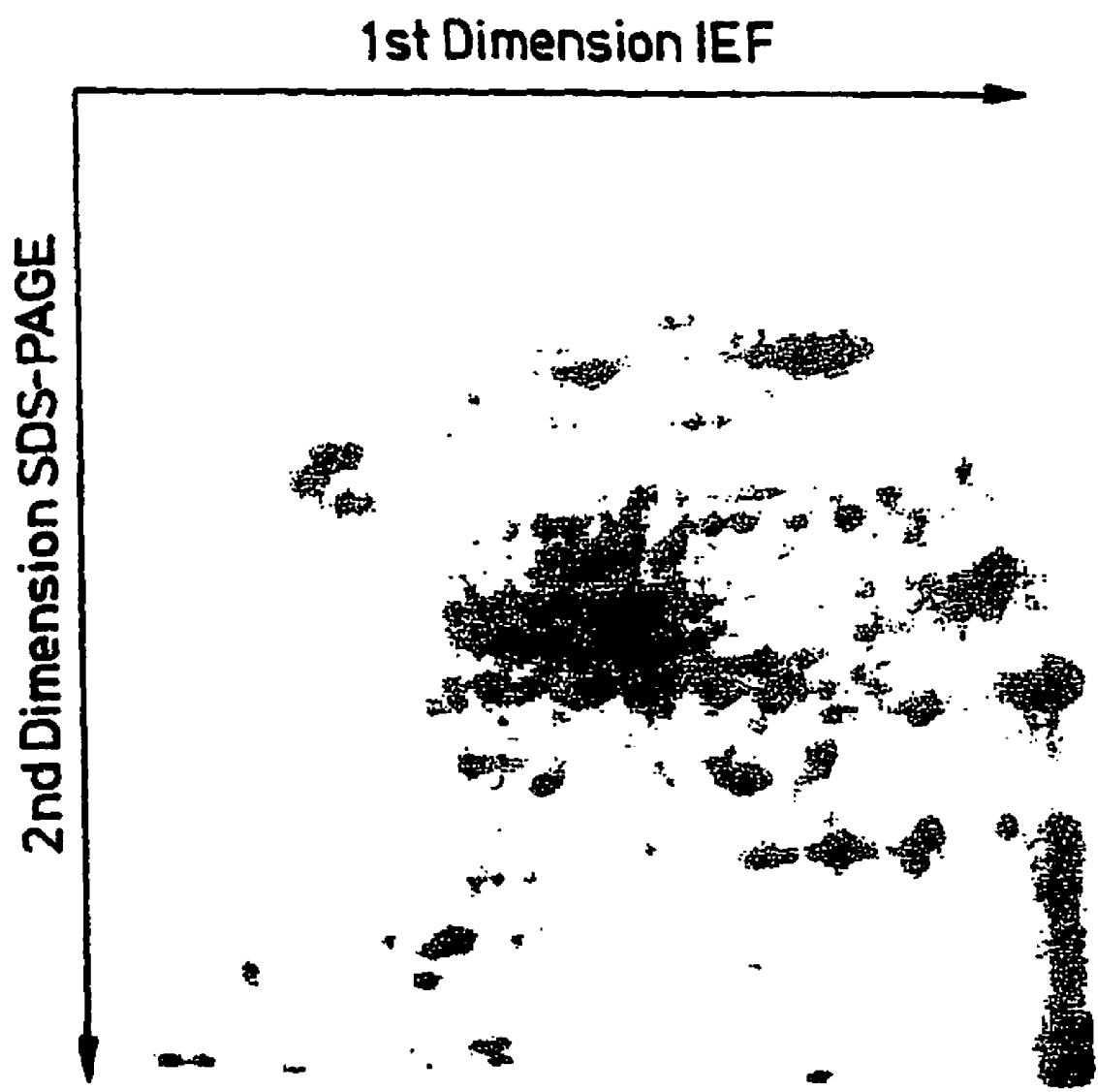
FIG. 7 shows the result of two-D separation of an $E.\ Coli$ lysate, where a total sample amount of 150 µg was loaded on an IEF strip of 7 cm, pH range 4-7, and the second dimension separation was executed according to a method based on SDS electrokinetic equilibration.

At this point the strip is coupled to the gel with the proteins focused in bands within the strip at their isoelectric points. This means however that carrying a zero net charge they won't be able to be transferred to the gel for the second dimension analysis. They have indeed been previously alkylated but are not yet complexed with Sodium-dodecyl-sulphate (SDS), which gives them a net negative charge and binds to them with a constant ratio allowing them to be separated now according to size through the sieving matrix of the gel. One way to bring SDS to the proteins is electrokinetically from the cathodic buffer reservoir. A concentration of SDS higher than that present in the running buffer is however necessary, e.g., 2% versus 0.1 or 0%. This has two implications: first the buffer at the cathode needs to be replaced or diluted after electrokinetic equilibration, second the distance of the strip from the buffer should in one embodiment be small (e.g., <5 mm) in order to minimize the zone at high SDS concentration entering the gel. The resulting effect is however superior to the standard procedure. As the SDS migrates into the gel and encounters the protein bands, these start to mobilize from the tail while the head is still steady. The result is a stacking effect with the bands gradually compacting at the opposite side of the strip before beginning their migration and separation inside the gel, which in turn means a gain in resolution. In that respect FIG. 7 shows the result of the two-D separation of an *E. Coli* lysate, where a total sample amount of 150 μg was loaded on an IEF strip of 7 cm, pH range 4-7, and the second dimension separation was executed according to the method based on SDS electrokinetic equilibration. The achieved resolution, shown in FIG. 7, appears clear to a person skilled in the field and was confirmed by mass spectrometry analysis, which proved also the absence of artifacts. Once proteins have complexed with SDS, the interaction is sufficiently strong so that no SDS needs actually to be present in the gel solution from the beginning. By this way we also make sure that no SDS diffuses into the strip from the gel solution causing partial complexation of the proteins and potentially disrupting the stacking effect described. SDS electrokinetic equilibration with the first buffer in one embodiment is carried out at lower electric fields compared to the separating conditions. For example, an electric field is applied in the range of approximately 5 to 6 v/cm or lower. This step takes approximately 5-10 min, the time necessary for the SDS to pass through the strip, after which the run is paused e.g., for the time necessary to replace the buffer, the buffer at the cathode replaced or diluted, if starting from a smaller volume, and the run restarted at much higher electric fields for fast separation, while the heat is dissipated through efficient cooling. The strength of the higher electric field is dependent on the system and in one embodiment is higher than e.g., approximately 20 volt per centimeter. If a higher electric field is applied, a higher cooling capacity of the system has to be applied. In one embodiment, the gel mold is closed from all sides between the two planes, e.g., by means of a squeezable frame as mentioned above in respect to FIGS. 5 and 6. The buffers contact the gel at two opposite edges of the mold and on the same plane, through two parallel slits, one of which positioned between the strip and one edge, and as close as possible to the strip for the reasons above. The slits are also in one embodiment closed to prevent more efficiently evaporation and drying of the strip and to avoid gel solution leaking during casting in the vertical position. The slits might be created for example only when and where needed by cutting, with a blade function integrated in the instrument, thinner linings, that represent physical integral parts of the disposable body, e.g., made by injection molding. The slits could be otherwise sealed by a porous membrane, e.g., polyethylene, PES (polyethersulfone), polypropylene, or PET, with the right thickness and porosity and which withstand the extrusion pressure of the gel during casting but are then wetted by the buffer containing SDS thus establishing electrical contact with the gel. The use of tapes or adhesive tabs in one embodiment is avoided, which is advantageous from an automation point of view.

Steps 8 and 9

From sample loading to this point all steps could be automated. Once the second dimension run is completed, the user can remove manually the disposable from the instrument and take the gel off. In one embodiment, for easier handling, the gel remains attached to one of the surfaces of the mold, either the disposable body or the covering plane, which can consist either of a rigid plate, e.g., glass or polymer, or a polymeric, more flexible foil. The surface where the gel sticks has to be consequently chemically accessible by polymerization process while the other has to be chemically inert towards the radical polymerization. The supported gel can be then processed according to the traditional procedure for fixing and staining.

The resolution in the second dimension is increased as a consequence of the stacking effect during the equilibration Steps 6 and 7. Prior alkylation and SDS elektrokinetic equilibration together eliminate the need of treating the strip with equilibration solutions between first and second dimension. This means avoiding handling or moving the strip or closing the strip with valves, avoiding extra buffers, avoiding the use of coupling agarose or other stacking gel, reducing the complexity of operation, either manual or automatic, saving time, which means also minimized band broadening by diffusion, hence increased resolution also for the first separation. Finally, eventual washing out of proteins that can occur when using equilibration solutions is no longer an issue. The use of a gel formulation, which can be quickly polymerized and is stable as long as an external light source is not applied, avoids problems associated with gel preparation, avoids the need of prepolymerizing the gel before IEF and separating it from the strip by means of barriers, and avoids otherwise long waiting times with consequently loss of resolution within the strip.

Below, new inventive gel electrophoresis embodiments, illustrated by FIGS. 8-11 are disclosed and the relative advantages highlighted. Part of the invention is however also another new method derived from the '975 application, by which two-dimensional IEF can be performed without the use of valves as a prefractionation step before coupling to a third-dimension gel electrophoresis. Thus no mention will be now made for e.g., the way in which sample loading, rehydration, IEF, equilibration and second dimension gel electrophoresis are carried out, since already described elsewhere or above.

Figure 8:
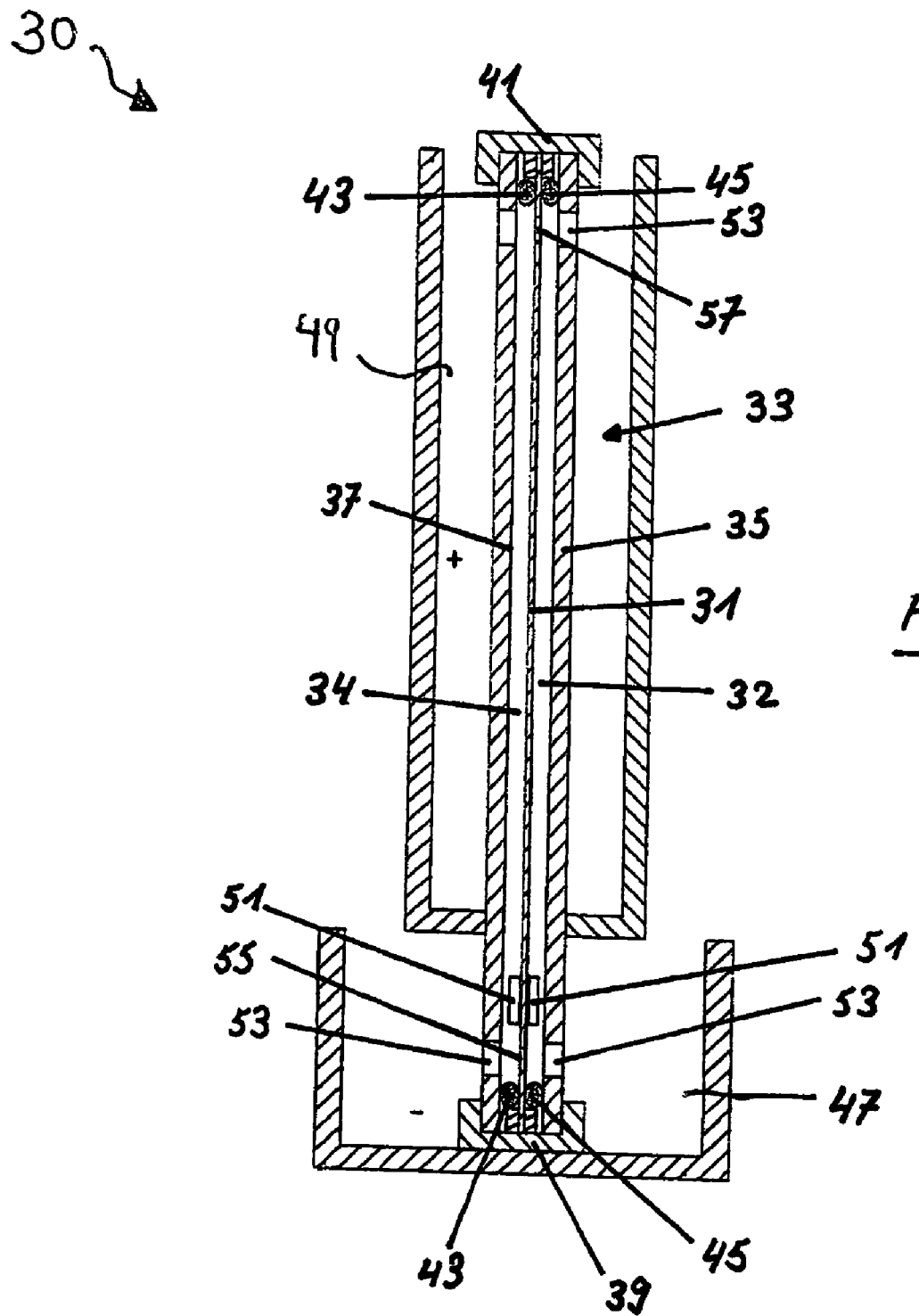
FIG. 8 is a block diagram, shown in cross section, of an embodiment according to the present invention which allows the running two separation steps of two-dimensional electrophoresis for two protein samples to be compared under nearly identical conditions as if they were run in a single gel like in the DIGE approach but without the need for pre labeling.
Figure 9:
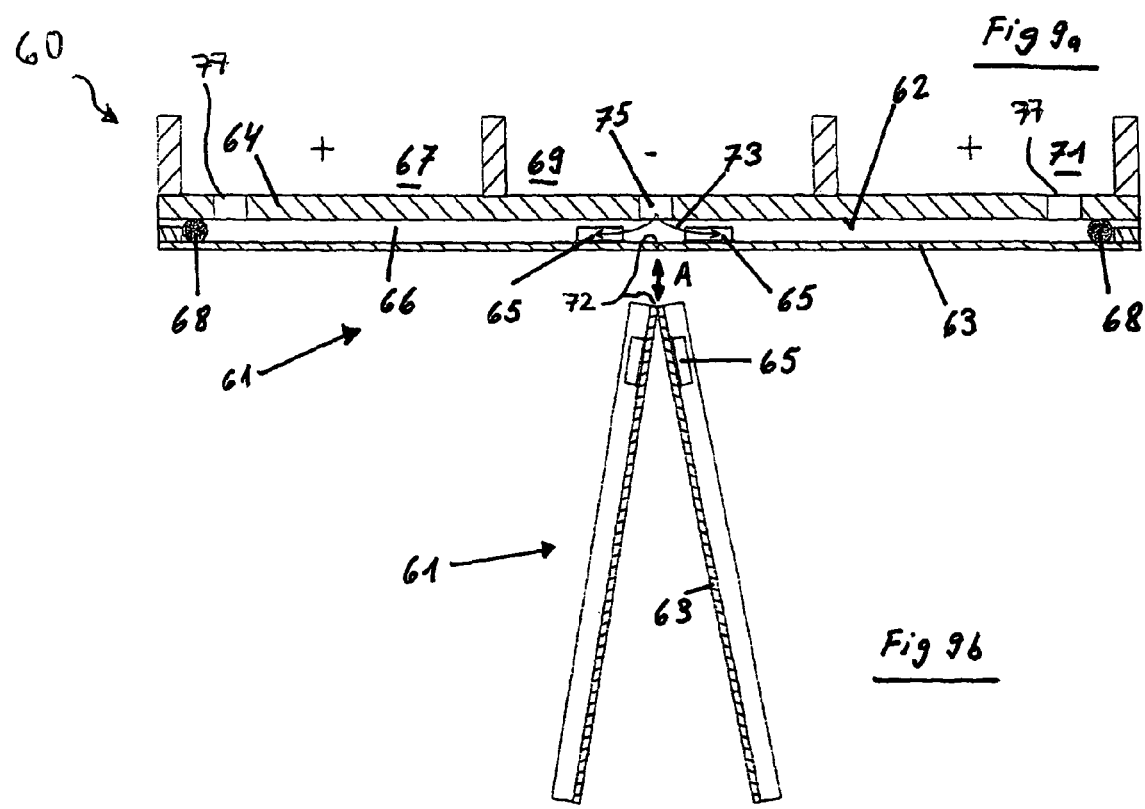

FIG. 8 shows one possible embodiment of a gel electrophoresis device, which is indicated generally by symbol 30, as an example of the present invention in a form called "mirror gels". In this embodiment as shown in FIG. 8, a gel electrophoresis mold 33 has a central or middle UV and visible light transparent carrier 31, such as a film, foil, or the like, provided in a sandwich or cassette-like arrangement between two external gel surface covers or plates 35 and 37. The distance between the two plates 35 and 37 can vary so that the distance between each of their internal surfaces and the central carrier 31 can assume the values e.g., of about 0.7 mm to about 1 mm depending on applied external pressure. For example, in the illustrated embodiment, the applied external pressure is provided by a system of clamps 39 and 41 positioned at each side and end of the carrier 31, which compresses a system of compressible gaskets 43 and 45 to provide the desired distance between the carrier 31 and plates 35 and 37. In addition to the gel electrophoresis mold 33, the device 30 includes buffer reservoirs 47 and 49. The device 30 can be injection molded using a light and/or UV transparent material and be all or partly disposable. The light and/or UV transparency of the device 30 is important due to the reason that for the formation of the gel for the separation in the second dimension, UV or light activated polymerization is used, which takes place within the two chambers 32 and 34 formed between the carrier 31 and the two plates 35 and 37.

Two identical first gel strips 51 are attached and aligned at a position in correspondence of each other on either side of the carrier 31, a characteristic of which is to have gel bond properties on both sides. In one embodiment, these first gel strips 51 are made out of a hydrophilic gel material as described in the '975 application. In other embodiments, the first gel strips 51 are immobilized pH gradient isoelectric focusing (IPG-IEF) gel strips. In mirror configuration are also slits 53 on the external plates 35 and 37 at the gel/buffer interfaces, for which the same reasoning can be applied as also previously disclosed e.g., concerning the use of membranes. Another feature of the carrier 31 is that a series of holes 55 and 57 is provided along two lines parallel to the strips 51 and at the two very extremities of the gel electrophoresis mold 33 with the function to allow liquid communication between the two chambers 32 and 34 at each side of the foil 31. In this way the two chambers 32 and 34 are filled simultaneously and homogeneously upon providing the gel solution therein. Polymerization of the gel solution is also accomplished simultaneously in both chambers 32 and 34 by shortly shining e.g., UV light of appropriate wavelength and power from both sides of the mold 33 as proposed within step 5 mentioned above; and this is the same advantageous also when casting gradient gels.

The embodiment as shown in FIG. 8, beside all the advantages of the general method, allows running the two separation steps of two-dimensional electrophoresis for two protein samples to be compared under nearly identical conditions as if they were run in a single gel like in the DIGE approach but without the need for pre labeling. Protein spots will theoretically form 2D mirror patterns on both sides of the transparent carrier 31 through which they can then be directly compared after visual staining. More experiments could be made for control with different combinations of the two samples, e.g., sample 1 versus sample 1, sample 2 versus sample 2, and of course sample 1 versus sample 2.

A further embodiment of another gel electrophoresis device, which is indicated generally by symbol 60, as a further possible example according to the present invention is shown in FIGS. 9a and 9b in a form called "symmetric gels." FIG. 9a shows the arrangement according to the present invention in a longitudinal section during the separation of the sample in the first and second dimensions and FIG. 9b shows the gel strips after finishing the separation for analytical reason with the possibility to compare simultaneously the separation of two samples.

In the illustrated embodiment of FIG. 9a, the device 60 has a gel mold 61 providing a carrier 63, which is a similar material to carrier 31, with doubled area and gel bonding properties only on one side. Two first gel strips 65 are now attached and aligned parallel at a certain distance between them and equally distant from the central axis A of the gel mold 61 which now assumes a perfectly symmetrical shape. In this embodiment, there are three different buffer reservoirs 67, 69, and 71 for two gels, two anodes and one common cathode, integrated, in one embodiment, in an injection molded, UV transparent disposable body 64. In an alternative embodiment, the reservoirs are external, integrated instead in the instrument with the buffer made to recirculate. The distance between carrier 63 and the inner surface 62 of the disposable body 64 can vary also in this case during the different steps due to the arrangement of compressible gaskets 68, and when mated together two chambers 66 are defined in the device 60. Arrows 73 in FIG. 9a indicate the direction of movement of the SDS during electrokinetic equilibration between first and second dimension, which is through a central slit 75 provided in the body 64 and the gel strips 65 provided in chambers 66. Additional slits 77 in the body 64 are provided for the other buffer reservoirs 67 and 71. The two second dimension separations run within the two chambers 66 in opposite directions as also indicated by arrows 73. After separation of the sample in the first and second dimensions, the carrier 63 can be peeled off, stained and bent and folded over the midline equidistant from the two strips in order to achieve again in transparency easy and direct comparison, as shown in FIG. 9b. This can be achieved e.g., by arranging a groove or recess 72 in the middle of carrier 63.

Since homogeneous conditions can be guaranteed also in this case, the advantages are virtually the same as above. One unfavorable difference is the fact, that this embodiment is not suitable for casting gradient gels. One favorable difference is perhaps a simpler design with even lower cost of manufacture, certainly lower than for two separate single gel disposables.

Figure 10:
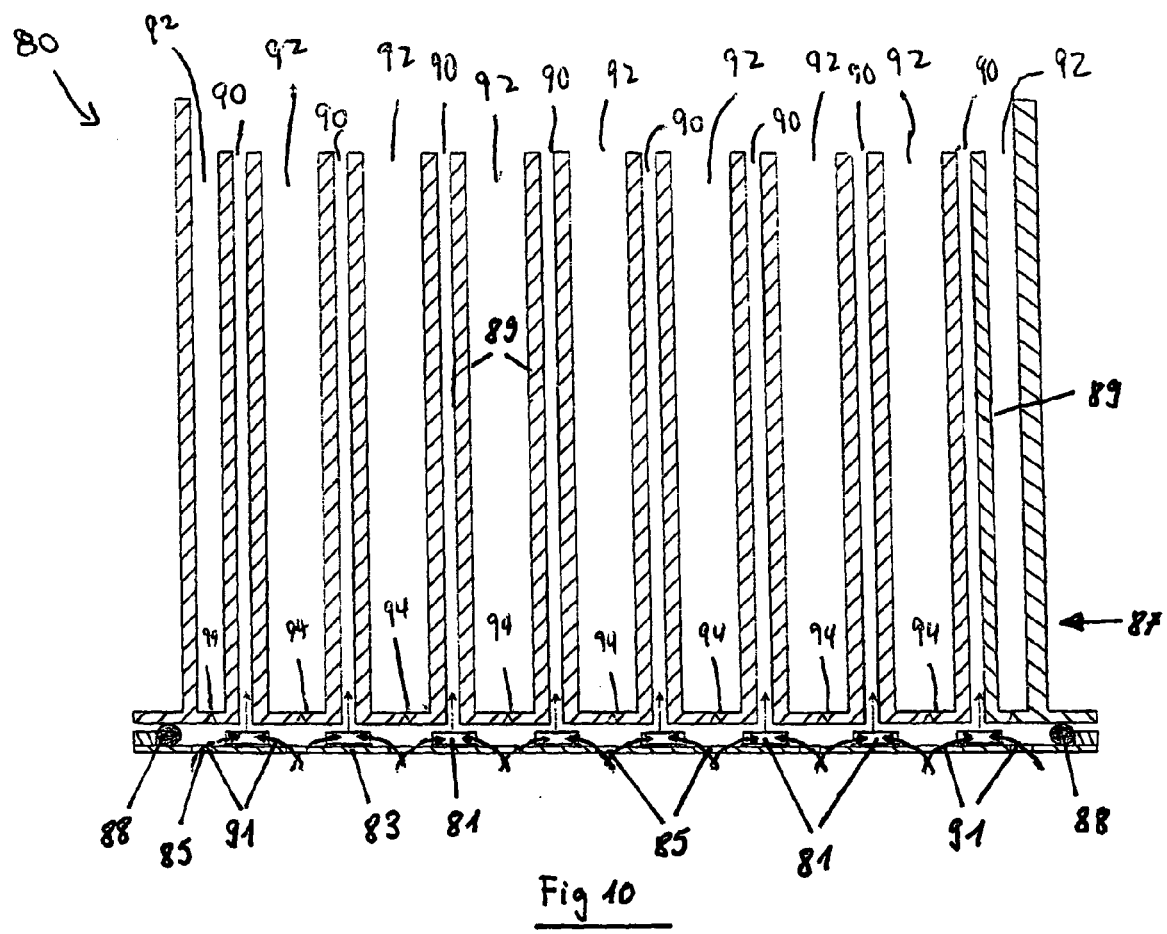
FIG. 10 is a block diagram, shown in cross section, of a further embodiment according to the present invention, which is shown in a "parallel gels" form.

Again a further embodiment of another gel electrophoresis device, which is indicated generally by symbol 80, as a further example according to the present invention is shown in FIG. 10 in a form called "parallel gels." With this embodiment a number of first gel strips 81 ($\geq 2$) is arranged parallel equally distant and perfectly aligned with each other on a flat and thin carrier 83, which is a similar material to carrier 31, through which a series of slits 85 also parallel to the strips and equally distant from each strip are also arranged at the interface with the external buffer (not shown). The strips 81 can be either identical to run different samples or replicas of the same samples in parallel or can carry different pH ranges for zoomed separations after e.g., a prefractionation step. At the perimeter of the carrier 83 use is made again of compressible caskets 88, on top of which e.g., a block 87 is clamped. The block 87 consists of parallel vertical gel molds 89 (e.g., 1 mm spacing 94) for arranging second gel strips 90 for the separation in the second dimension, equally spaced to stand in correspondence of the first gel strips 81 underneath. The space in between is represented by cavities 92 to be filled with the anodic running buffer until covering the gel molds 89. Although this is a single piece block injection molded once again with light or UV transparent material, features are inserted along the edges of the buffer cavities 92 so that the block 87 can be easily disassembled at the end of the analysis by weak manual torsion allowing opening of the individual gel molds 89 for gel strip removal. The arrows 91 in FIG. 10 indicated again the shape of the electric field, the direction of movement of the SDS during electrokinetic equilibration with stacking towards the center of each strip 81 and subsequent protein transfer and migration into the vertical gel strips 90. Again reference is made to the previously described steps in relation to the '975 application.

Again the main advantage over individual single gel analyses is to have more homogeneous conditions for several gels simultaneously so that higher reproducibility can be expected between them. Also remarkable reduction in the complexity of the system and operation is obtained compared to the handling of single strips and single gels, providing a really convenient straight forward approach for coupling strips in a tray to the second dimension separation. It should be noted also that this embodiment according to FIG. 10 is amendable also to the classical method of running IEF, e.g., under mineral oil and to equilibrate the strips with standard equilibration solutions between first and second dimension.

Figure 11A:
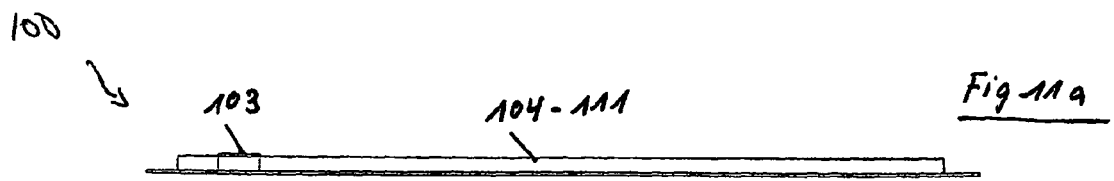
Figure 11B:
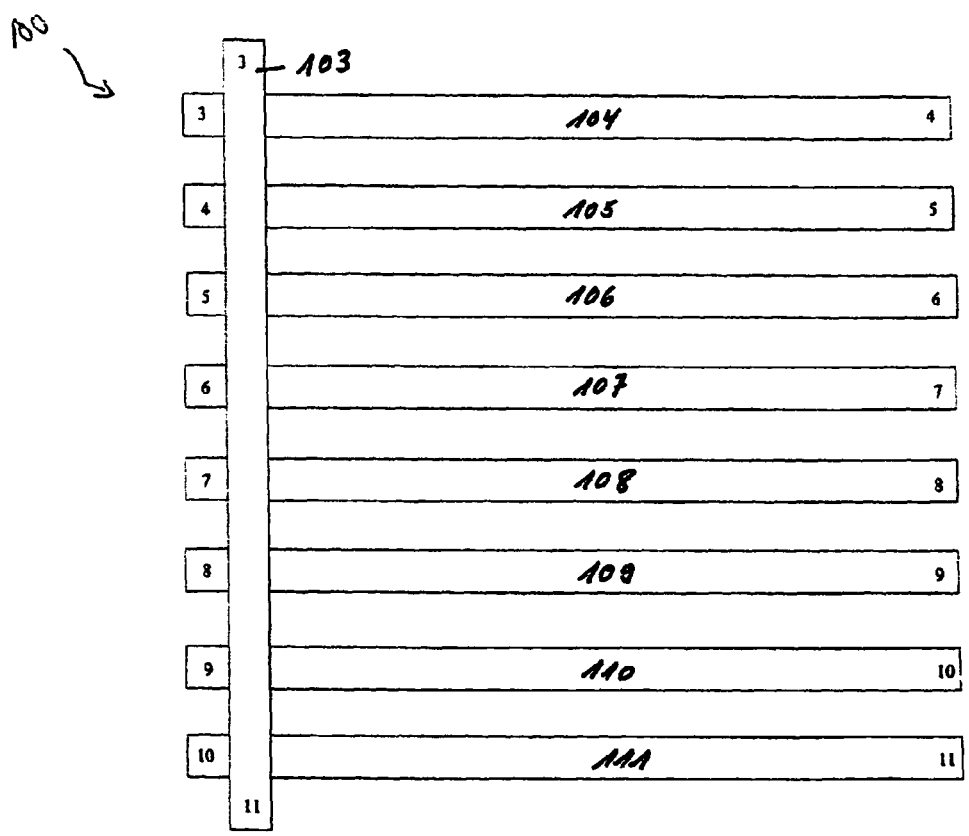

Finally, a further embodiment of another gel electrophoresis device, which is indicated generally by symbol 100, allows extension from two- to three-dimensional analyses as shown in FIGS. 11a and 11b. FIG. 11a shows the embodiment for the first dimension separation in cross sectional view and FIG. 11b shows the embodiment for the first separation in view from above.

The fact that the strip rehydration and focusing can occur without any valves or barrier means makes it possible to couple different strips passing, e.g., from a broad pH range immobilized pH gradient (IPG) strip to a narrow pH range IPG strips as in FIG. 11. It is indeed possible to run IEF for the first strip 103 long enough to allow prefocusing and protein distribution along the pH range, but short enough for the proteins to be still charged before reaching their isoelectric points. In this way, after coupling to the parallel strips e.g., 104-111 ordered according to a pH range ladder, proteins can be transferred and separated orthogonally, thus achieving fractionation in the first dimension and increased resolution in the second dimension.

Thanks to faster polymerization and in one embodiment to SDS electrokinetic equilibration, the device 100 as shown in FIGS. 11a and 11b can therefore be combined with the device 80 shown in FIG. 10 where the various individual gel molds as designated with the referential number 89 are being arranged each above one of the parallel strips 104 to 111 and the separation in the third (before second) dimension can be carried out.

The embodiments as shown in FIGS. 8-11 are only examples for the description and the better understanding of the present invention. Compared with the gel electrophoresis disposables as disclosed within the '975 application, according to the present invention at the same time two or more separations of analytical mixtures are possible due to the fact, that within the '975 application a simpler and better electrophoresis separation method to be automated is disclosed using disposable bodies without the need of the arrangement of valves.

The present invention is of course not at all limited to the embodiments as shown in FIGS. 8-11 and any development based upon the '975 application disclosing the use of at least two first gel strips and respectively executing in parallel at least two separation processes for at least two samples using electrophoresis is falling under the scope of the present invention.

What is claimed is:

1. A device providing an arrangement for separation of a complex protein sample based on multidimensional gel electrophoresis without the use of valves, the separation involving a first separation of the sample on the basis of isoelectric points and a second separation of the sample on the basis of molecular size, said device comprising:
   at least two first gel strips which provide for the first separation in a first dimension of the device;
   a single carrier supporting said first gel strips such that at least two analytical processes each involving the first separation and the second separation can be executed in parallel on said single carrier; and at least one opposite disposable surface provided in a first position from said single carrier, wherein when in said first position the surface is in contact with said first gel strips and moveable to a second position which provides a gap between said first gel strips and said surface such that a gel contacts each of said first gel strips and provides for the second separation in a second dimension of the device, and wherein at least two analytical processes each involving the first separation and the second separation can be executed in parallel.

2. The device according to claim 1, wherein said first gel strips are provided on a same side of said single carrier.

3. The device according to claim 1, wherein said first gel strips are provided on opposite sides of said single carrier.

4. The device according to claim 1, wherein said first gel strips are arranged symmetrically on said single carrier.

5. The device according to claim 1, wherein said first gel strips are arranged in parallel on said single carrier.

6. The device according to claim 1, wherein said first gel strips are hydrophilic, such that introduction of the sample into the device occurs by hydrophilic guiding.

7. The device according to claim 1, wherein said at least one opposite disposable surface being coated at least partly with one of a hydrophobic or non gel sticking material, on a side of the gel strips and not directly in correspondence of the gel strips.

8. The device according to claim 1, wherein the opposite disposable surface is provided by a disposable body.

9. The device according to claim 1, wherein the opposite disposable surface is provided by at least one plate.

10. The device according to claim 1 further comprising compressible gaskets provided between the carrier and at least one plate provided a distance adjacent said at least two first gel strips.

11. The device according to claim 1, wherein said device is at least partly UV and visible-light transparent.

12. The device according to claim 1, wherein said device is valveless.

13. The device according to claim 1 further comprising a pair of plates enclosing the at least two first gel strips and the single carrier there between.

14. The device according to claim 1, wherein the single carrier is a foil with gel-bond properties.

15. The device according to claim 1 further comprising buffer reservoirs, a pair of plates enclosing the first gel strips, and clamps holding the pair of plates in position and at a desired distance relative to the single carrier, the plates also comprising holes for introduction of a formulating solution of the gel and slits at interfaces of the gel with said buffer reservoirs.

16. The device according to claim 1 further comprising a series of holes located along the single carrier to allow liquid communication between both sides of said single carrier.

17. The device according to claim 1 further comprising compressible gaskets and a disposable body having a cover surface which provides the opposite disposable surface, wherein the first gel strips are attached on the same side of the single carrier and are aligned equally distant from a central axis of the single carrier, the single carrier with the two first gel strips being closed by the cover surface of the disposable body, wherein a distance between the single carrier and the cover surface is variable during different steps of the electrophoresis due to the compressible gaskets being provided between the single carrier and the cover surface, and expandable when moving the opposite disposable surface from said first position to said second position.

18. The device according to claim 17, wherein the single carrier is transparent and has a groove along the central axis such that after the separation of the sample, the single carrier can be removed from the disposable body, taking with it the gel and the first gel strips, can be bent at the groove and folded over about the central axis in order to achieve in transparency easy and direct comparison of the separated samples.

19. The device according to claim 17 further comprising one central anodic reservoir and two opposing cathodic reservoirs, wherein the cover surface of the disposable body has a respective slit for each of said reservoirs, and wherein SDS electrokinetic equilibration for separations in the second dimension proceed in opposite directions.

20. The device according to claim 1, wherein said first gel strips are arranged in parallel and equally distant from each other, and aligned with each other on one side of the single carrier through which a series of slits also parallel to the first gel strips and equally distant from each strip are provided.

21. The device according to claim 20 further comprising a compressible gasket provided adjacent a perimeter of the first gel strips, and a disposable body provided on said compressible gasket, said disposable body comprising parallel vertical gel molds which provide for the separations in the second dimension, said vertical gel molds are equally spaced to stand in correspondence of the first gel strips underneath, the gel molds being made of a transparent material.

22. The device according to claim 21, wherein between the vertical gel molds grooves are provided so that the vertical gel molds individually can easily be disassembled from the disposable body.

23. The device according to claim 21 further comprising a second gel strip in contact with said first gel strips, said second gel strip allowing a separation in a third dimension of said device.

24. The device according to claim 1 further comprising a second gel strip provided in contact at one side with and nearly perpendicular to the first gel strips, said second gel strip providing a first quick separation of the sample in a broad pH range such that, the proteins of the sample are still charged before reaching their isoelectric points, and wherein said first gel strips represent a pH ladder each corresponding to a narrow pH range comprised within the broad pH range of the second gel strip, so that transfer of zones from the second gel strip to the respective first gel strips can occur, whereby increased resolution can be obtained.

25. The device according to claim 1, wherein said first gel strips are arranged in parallel and equally distant from each other, and aligned with each other on one side of the single carrier through which a series of slits also parallel to the first gel strips and equally distant from each strip are provided, further comprising a second gel strip provided in contact at one side with and nearly perpendicular to the first gel strips, said second gel strip providing a first quick separation of the sample in a broad pH range such that, the proteins of the sample are still charged before reaching their isoelectric points, and wherein said first gel strips represent a pH ladder each corresponding to a narrow pH range comprised within the broad pH range of the second gel strip, so that transfer of zones from the second gel strip to the respective first gel strips can occur, whereby increased resolution can be obtained.

26. The device according to claim 25, further comprising a compressible gasket provided adjacent a perimeter of the first gel strips, wherein the opposite disposable surface is provided by a disposable body provided on said compressible gasket, said disposable body comprising parallel vertical gel molds for the gel to provide for the separations in the second dimension, said vertical gel molds are equally spaced to stand in correspondence of the first gel strips underneath, the gel molds being made of a transparent material.

27. The device according to claim 26, wherein between the vertical gel molds grooves are provided so that the vertical gel molds individually can easily be disassembled from the disposable body.

28. The device according to claim 1, wherein the opposite disposable surface is provided by a fitting bar of a disposable body.

29. A method for separation of a complex protein sample based on multidimensional gel electrophoresis without the use of valves, the separation involving a first separation of the sample on the basis of isoelectric points and a second separation of the sample on the basis of molecular size, said method comprising:
   providing the first separation in a first dimension using at least two first gel strips;
   providing the second separation in a second dimension using a gel in contact with each of said at least two first gel strips;
   supporting said first gel strips and said gel on a single carrier such that at least two analytical processes each involving the first separation and the second separation can be executed in parallel on said single carrier; and
   providing at least one opposite disposable surface a distance from said single carrier, wherein after separation in the first dimension the distance between the single carrier and the at least one opposite disposable surface is increased to provide optimal conditions for gel casting, polymerization, SDS equilibration, transfer and separation into the gel in the second dimension.

30. The method according to claim 29, wherein said gel is provided by UV gel polymerization of a gel forming solution.

31. The method according to claim 29 further comprising providing a flat sealing cover to the single carrier until the first dimension separations are completed, and then substituting said flat sealing cover with a disposable body before proceeding with gel casting, polymerization and second dimension separations, said disposable body comprising parallel vertical gel molds which provide for the separations in the second dimension, said vertical gel molds are equally spaced to stand in correspondence of the first gel strips underneath.

32. The method according to claim 29 further comprising providing a second gel strip in contact at one side with and nearly perpendicular to the first gel strips, said second gel strip providing a first quick separation of the sample in a broad pH range such that, the proteins of the sample are still charged before reaching their isoelectric points, and wherein said first gel strips represent a pH ladder each corresponding to a narrow pH range comprised within the broad pH range of the second gel strip, so that transfer of zones from the second gel strip to the respective first gel strips can occur, whereby increased resolution can be obtained.

33. The method according to claim 32 further comprising providing a compressible gasket adjacent a perimeter of the first gel strips, and providing a disposable body provided on said compressible gasket, said disposable body comprising parallel vertical gel molds which provide for the separations in the second dimension, said vertical gel molds are equally spaced to stand in correspondence of the first gel strips underneath, wherein said second gel strip provides for a separation in a third dimension.

* * * * *